(12) United States Patent
Dickie

(10) Patent No.: US 6,295,996 B1
(45) Date of Patent: Oct. 2, 2001

(54) DENTAL FLOSS DISPENSER

(75) Inventor: Robert G. Dickie, Newmarket (CA)

(73) Assignee: Spark Innovations Inc.

( * ) Notice: Subject to any disclaimer, the term of this patent is extended or adjusted under 35 U.S.C. 154(b) by 0 days.

(21) Appl. No.: 09/625,172

(22) Filed: Jul. 25, 2000

(51) Int. Cl.[7] .................................................. A61C 15/04

(52) U.S. Cl. .......................................... 132/321; 206/63.5

(58) Field of Search ...................................... 132/322, 323, 132/324, 325, 328, 329, 321; 206/63.5, 408, 409; 242/138, 137.1, 146, 588.6, 598.6; 248/683; D28/65, 66, 67, 68

(56) References Cited

U.S. PATENT DOCUMENTS

| | | | |
|---|---|---|---|
| D. 311,259 | * 10/1990 | Smith | D28/64 |
| 3,480,190 | * 11/1969 | Freedman | 225/33 |
| 4,881,560 | 11/1989 | Blank et al. | |
| 5,054,674 | * 10/1991 | Fortman | 225/6 |
| 5,076,423 | 12/1991 | Russack . | |
| 5,156,311 | 10/1992 | Spencer, Jr. et al. . | |
| 5,160,077 | * 11/1992 | Sticklin | 225/38 |
| 5,282,563 | 2/1994 | Oliver et al. . | |
| 5,649,659 | 7/1997 | Saunders . | |
| 5,680,875 | * 10/1997 | Winters | 132/224 |
| 5,989,708 | * 11/1999 | Kreckel | 428/354 |

* cited by examiner

Primary Examiner—Todd E. Manahan
Assistant Examiner—David Comstock
(74) Attorney, Agent, or Firm—Marks & Clerk

(57) ABSTRACT

A dispenser for dental floss comprises a closed container having a reel of dental floss disposed therein, and having a generally planar back face, a front face, a pair of opposed side faces, a top face, a bottom face opposed to the top face, and a corner at each intersection of the top and bottom faces with the pair of opposed side faces. A hub is centrally located in the interior of the closed container and extends between the interior surfaces of the front and back faces. The reel of dental floss is mounted for rotation about the hub. There is an opening in the front face at a first corner, through which a strand of dental floss extends so as to be unwound from the reel; and a friction and cutting member is at a second corner of the front face. The friction and cutting member comprises a tongue portion which is angled away from a base portion, and is secured in place at the second corner of the front face. The front face is concave on an axis extending between a pair of diagonally opposed corners of the container, the concavity being defined by ridges formed in the front face at the first corner, and at a diagonally opposed corner. A C-shaped chute is formed at the second corner, and is positioned such that the dental floss extends from the opening at the first corner through the C-shaped chute located at the second corner.

19 Claims, 2 Drawing Sheets

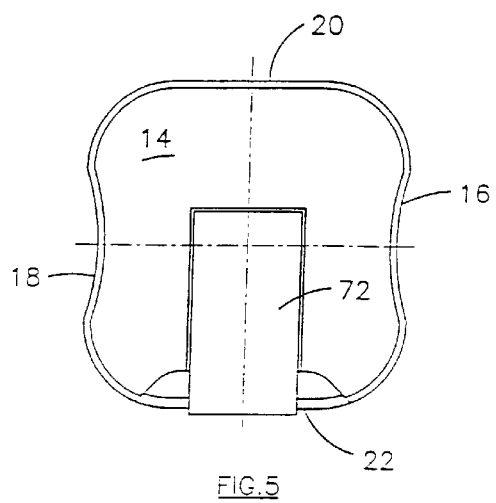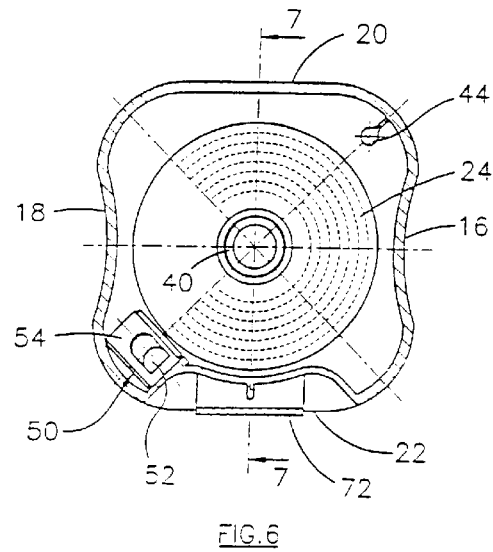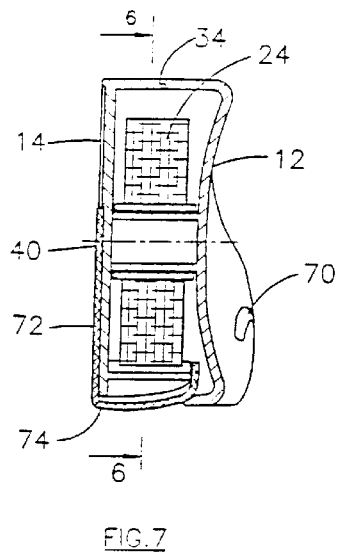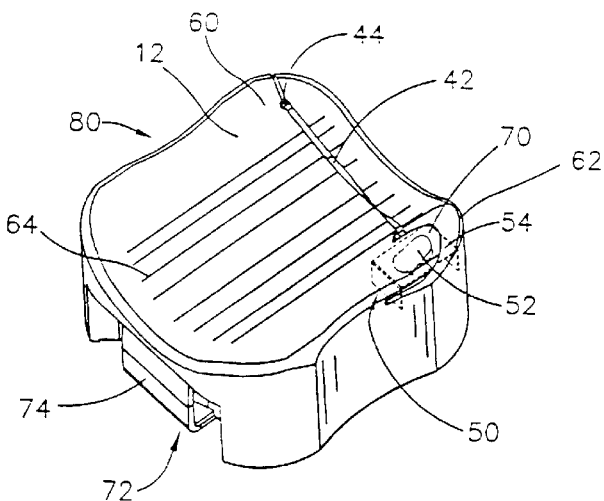

DENTAL FLOSS DISPENSER

FIELD OF THE INVENTION

The present invention relates to a dispenser for dental floss. In particular, the present invention provides a dispenser which may conveniently be, but not necessarily, mounted to a mounting surface. The mounting surface is preferably, but not necessarily, vertical. Especially when mounted to a mounting surface, dental floss may be removed from the dental floss dispenser using but a single hand.

BACKGROUND OF THE INVENTION

The use of dental floss is highly recommended by the dental profession as a necessary adjunct to oral hygiene. Indeed, the dental profession recommends that teeth should be flossed using an appropriate dental floss, at least once daily; for example and particularly, as part of the evening ablutions prior to retiring for the night.

Typically, dental floss is sold in a container which serves as the dispenser for the dental floss. Typically, when it is not actually being used to dispense dental floss, the container/dispenser is hidden away from view such as in a drawer, a medicine cabinet, or the like. This generally results in less than diligent flossing practice.

Indeed, recent studies reveal that only about 20 percent of the population of North America flosses regularly, although it is assumed that between 70 percent and up to 90 percent of all households have at least one dental floss container in their possession.

Moreover, it has been noted that there seems to be less of a tendency to want to use a dental floss dispenser which requires it to be held in one hand while dental floss is removed from the dispenser with the other hand, especially in those circumstances where the cutter for the dental floss is exposed and represents a risk to the fingers of the user. Still further it has been noted that most commercially available dental floss dispensers are awkward to use in that the spacing between the opening in the dispenser where the dental floss exits from the interior thereof to the cutter is generally quite small, so that grasping the dental floss in that region so as to remove a length of dental floss from the container is difficult.

For all of these reasons, the present invention provides a dental floss dispenser from which dental floss may be much more easily grasped so as to be removed from the dispenser. In certain embodiments of the present invention, there is provided a dental floss dispenser in which the cutter for the dental floss is hidden from view and is therefore not dangerous to the fingers of a person removing dental floss therefrom.

Still further, in certain embodiments of the dental floss dispenser of the present invention, the dental floss container or dispenser may be mounted on a mounting surface such as a bathroom mirror, inside a medicine cabinet door, on a wall in the bathroom or washroom, or other convenient and visible location. It has been noted that when a dental floss container is conveniently located in such a place and in such a manner that dental floss may be easily removed therefrom, it is more likely to be used, and therefore the practice of flossing one's teeth is much more diligent.

PRIOR ART

Blank et al U.S. Pat. No. 4,881,560, issued Nov. 21, 1989, provides a flat dental floss dispenser which has the approximate size and shape of a credit card. A flat coil of floss is located within the dispenser. However, the cutting blade is quite prominent, thus representing a danger to the fingers of the user. Moreover, to disengage the dental floss from the surface of the cover of the container in the region between the opening through which the dental floss is dispensed and the cutter from which it is removed from the dispenser, requires that the dental floss be effectively pried away from the surface of the container using the fingernails.

Fortman, U.S. Pat. No. 5,054,674, issued Oct. 8, 1991, teaches a dispenser system including a dental floss dispenser which may be retained on or attached to a surface. The dispenser comprises a cassette of dental floss, and a supporting member. The supporting member may be attached to a surface such as a bathroom wall, and may serve other purposes as well such as functioning as a toothbrush holder. However, in this case, notwithstanding that the holder or support member is mounted to a wall, the dental floss dispenser is a separate cassette installed into the holder, and removal of dental floss from the container requires the use of two hands.

Russack, U.S. Pat. No. 5,076,423, issued Dec. 31, 1991, provides a relatively flat, wallet-sized dental floss dispenser. Here, once again, the cutter for the dental floss is prominently mounted over the surface of the container, representing a threat to the fingers of the user. Moreover, once again, the disengaging of dental floss so as to remove a length thereof from the dispenser is awkward, requiring reasonable dexterity with the fingers of the hand of the user.

U.S. Pat. No. 5,156,311, issued Oct. 20, 1992 to Spencer Jr., et al, teaches a dispenser which has a cover and a back section, together with a front section, all of them being molded and hinged together so as to permit the dental floss which is contained therein to be replaced. A shoulder saddle is provided, across which the dental floss is disposed. However, the cutter for the dental floss is prominently located as well on the saddle. Moreover, the configuration of the dispenser, having a hinged cover, requires the use of two hands to remove dental floss from the dispenser, and precludes the possibility that the dispenser can be mounted to such as a vertical, or any, surface.

Oliver et al, U.S. Pat. No. 5,282,563, issued Feb. 1, 1994, teaches a dental floss dispenser having a body which has a spool holder for holding a spool of dental floss at one end, and an exposed cutting member and friction element at the other end of the body. Dental floss is suspended between the spool holder and the cutter, the purpose being so that a user can grasp an exposed portion of floss without contacting any part of the floss dispenser and thereby contaminating the floss dispenser. Particularly, therefore, the floss dispenser described in this patent is one which is intended for use by dentists and dental hygienists, and is not proposed for use by private individuals in their own bathrooms. Various embodiments are illustrated, whereby the dispenser may be mounted on surfaces such as the underside of a table; but in each instance, the purpose is to provide a dental floss dispenser for use by a dentist, a dental assistant, or dental hygienist, in such a manner that the base of the dispenser is not contacted by the fingers of the professional dental caregiver.

Saunders, U.S. Pat. No. 5,649,659 issued Jul. 22, 1997 provides a dental floss dispenser which, again, has essentially the size and shape of a credit card. A spool of floss is wound in the interior of the dispenser, and is dispensed through an opening formed in the dispenser. In one embodiment a recess is formed in the major flat face of the dispenser, having the hole through which the dental floss exits from the interior of the dispenser at one end of the recess, and a cutter/holder disposed at the other end of the recess. In that manner, the cutter, the aperture, and the lead-out portion of dental floss between the opening and the cutter, are all disposed below the major face. In another embodiment, a fan-folded spool of floss is located inside the container, and exits through a hole at one end of the container. A dished top end of the container is provided, across which the lead-out portion of the dental floss extends to an exposed metal cutter assembly.

SUMMARY OF THE INVENTION

The present invention provides a dispenser for dental floss, which comprises a closed container having a reel of dental floss disposed therein. The container has a generally planar back face, a front face, a pair of opposing corners, side faces, a top face, a bottom face opposed to the top face, and a corner at each intersection of the top and bottom faces with the pair of opposed side faces. There is a hub which is centrally located in the interior of the closed container, and which extends between the interior surfaces of the front and back faces thereof, in the region of occupied by the hub. A reel of dental floss is mounted for rotation about the hub, when dental floss is unwound and removed from the reel.

There is an opening in the front face of the container at a first corner thereof, through which opening a strand of dental floss extends so as to be unwound from the reel. A friction and cutting member is found at a second corner of the front face; and the friction and cutting member comprises a tongue portion which is angled away from the base portion. The friction and cutting member is secured in place at that second corner.

The front face of the container is concave on an axis which extends between a pair of diagonally opposed corners of the container, the concavity thereof being formed by ridges which are formed in the front face at the first corner and at a corner of the front face which is diagonally opposed to the first corner.

A C-shaped chute is formed at the second corner, and is positioned such that dental floss extends from the opening of the first corner through the C-shaped chute located at the second corner. In some embodiments of the present invention, the second corner is adjacent the first corner.

In other embodiments of the present invention, however, the second corner is diagonally opposed to the first corner.

In either embodiment, the friction and cutting member may be secured in place in the interior of the container, at the second corner thereof, and at the interior surface of the front face. Indeed, the friction and cutting member may be located in the bight of the C.

Especially, where the concavity of the front faces is defined by the ridges formed in the front face at the first and second corners, those corners being diagonally opposed one to the other, then the C-shaped chute is formed in the ridge at the second corner and the friction and cutting member is located in the bight of the C.

In general, the container of the dental floss dispenser of the present invention may be molded from a plastics material, and the friction and cutting member is formed from metal.

In keeping with a further provision of the present invention, adhesive means may be placed on the substantially planar back face of the container for the dental floss dispenser, so that the dental floss dispenser may be adhesively mounted to a mounting surface.

Generally, the adhesive means comprises a flexible plastic tape which has an adhesive coating on at least a portion of each of the two sides thereof. Typically, the plastic tape is stretchable, and the second portion on each of the two sides of the plastic tape has no adhesive coating thereon, so that the uncoated portion of the flexible plastic tape forms a graspable tab to facilitate the removal of the dental floss dispenser from a mounting surface when it is adhered thereto.

As suggested above, typically the mounting surface is a vertical surface, such as a bathroom mirror, the inside surface of a medicine cabinet door, and so on.

In particular embodiments of the present invention, there may be a further plurality of ridges which are formed on the front face of the container, each of which plurality of ridges is formed in a direction parallel to the axis which extends between a pair of diagonally opposed corners of the container—neither of which corners is the first corner.

So as to assist the dispensing of dental floss, a guide wall therefor is located in the interior of the container. Thus, a dental floss dispenser in keeping with the present invention may have a guide wall which extends inwardly from the interior surface of the front face in the vicinity of the opening at the first corner. The guide wall is positioned inwardly from the opening, towards the hub.

An object of the present invention is to provide a dispenser for dental floss which permits dispensing of dental floss easily, where the dental floss is guided through a chute, and wherein a certain amount of concavity may exist between the opening where the dental floss exits from the interior of the dental floss dispenser and the chute through which it is guided.

A further object of the present invention is to provide such a dispenser for dental floss as described above, which may be easily and inexpensively brought to the market.

Yet a further object of the present invention is to provide such a dental floss dispenser as described above, where the dental floss dispenser may be secured to a mounting surface, and where removal of the dental floss from the dispenser may be easily effected using only a single hand. Typically, the mounting surface to which a dental floss dispenser in keeping with the present invention may be mounted, is a vertical surface.

BRIEF DESCRIPTION OF DRAWINGS

The novel features which are believed to be characteristic of the present invention, as to its structure, organization, use and method of operation, together with further objectives and advantages thereof, will be better understood from the following drawings in which a presently preferred embodiment of the invention will now be illustrated by way of example. It is expressly understood, however, that the drawings are for the purpose of illustration and description only and are not intended as a definition of the limits of the invention. Embodiments of this invention will now be described by way of example in association with the accompanying drawings in which:

FIG. 5 is a plan view, looking at the back face of a dental floss dispenser in keeping with the present invention;

FIG. 6 is a plan sectional view, looking in the direction of arrows 6—6 in FIG. 7;

FIG. 7 is a sectional view, looking in the direction of arrows 7—7 in FIG. 6; and FIG. 8 is a view similar to FIG. 1, but showing an alternative embodiment of the present invention;

DESCRIPTION OF THE PREFERRED EMBODIMENTS

Figure 1:
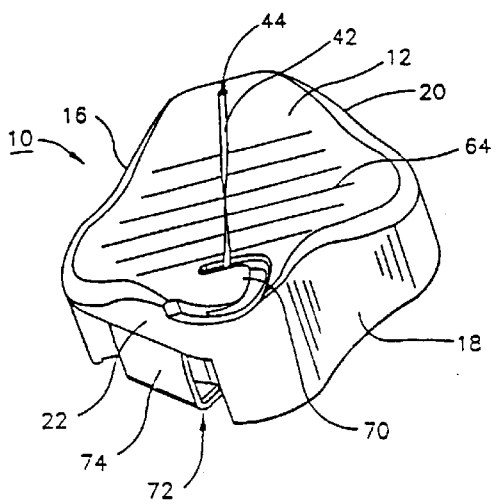
FIG. 1 is a perspective view of a first, preferred embodiment of the present invention.

It will be noted that there are several embodiments and features of the present invention, in respect of which the following discussion is made. Several features, as described hereafter, may or may not be found in any one embodiment of a dental floss dispenser in keeping with the present invention, so the discussion of any one feature with respect to any one embodiment is not mutually exclusive to any other feature which may or may not appear in the same embodiment or another embodiment.

In that regard, therefore, the following brief discussion is directed to several principal features of dental floss dispensers in keeping with the present invention.

The first principal feature is that the front face of any dental floss dispenser in keeping with the present invention has a concavity which extends between a pair of opposed corners, and is defined by ridges formed at the intervening corners. Still further, a first corner of the front face is one of the corners at which one of the opposed ridges is formed; and it is also the corner at which there is an opening through which a strand of dental floss will extend so as to be unwound from a reel internally located within the dental floss dispenser.

The strand of dental floss will extend from the opening at the first corner to a second corner, and to a friction and cutting member located at the second corner. However, the second corner may be diagonally opposed to the first corner, as is particularly shown in FIGS. 1 to 4, and 6; or the second corner may be adjacent the first corner, as is particularly shown in FIG. 8.

Moreover, the friction and cutting member which is located at the second corner, whether that corner which is diagonally opposed to or adjacent the first corner, is generally but not necessarily located in the interior of the container at the interior surface of the front face. For example, the friction and cutting member might be located on a side or bottom face of the dispenser container, as suggested in FIG. 8, or it might be located on the front face of the dental floss container—in a location which is not specifically indicated in any of the Figures, but which will be evident to those skilled in the art. On the other hand, there is at least a C-shaped chute formed at the second corner, no matter which location the second corner has, through which the dental floss extends from the opening at the first corner. This provides for a guide for the dental floss.

Therefore, typically, but not necessarily, the cutter and friction member is concealed beneath the C-shaped chute, so that the friction and cutting member located in the bight of the C.

Turning now to FIGS. 1 to 4, and FIGS. 6 and 7, several features of a first general embodiment of dental floss dispenser in keeping with the present invention are shown. The particular features are that, in this embodiment, the first and second corners—that is the corners at which the opening in the front face through which a strand of dental floss extends so as to be unwound, and the corner at which the friction and cutting member is located—are diagonally opposed one to the other. A dispenser 10 is illustrated, having a front face 12, a back face 14, a pair of opposed side faces 16, 18, a top face 20, and a bottom face 22. The container is a closed container. There is disposed within the closed container, however, a reel 24 of dental floss. The closed container of the dental floss dispenser 10 may comprise 2 half shells indicated at 30 and 32 in FIG. 4, which are sealed together in any convenient manner at the seam 34 which is formed around the container in the side faces 16, 18 and the top and bottom face 20, 22, respectively.

Figure 4:
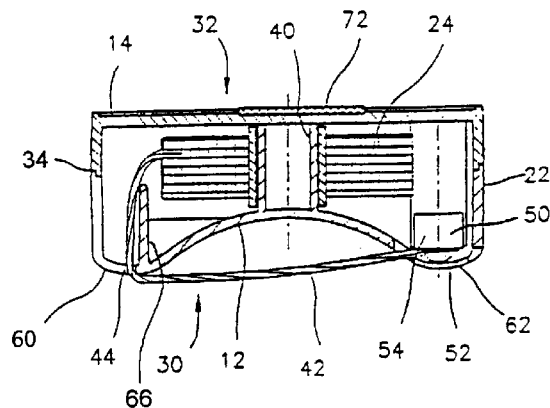
FIG. 4 is a sectional view, looking in the direction of arrows 4—4 in FIG. 3.

The reel of dental floss 24 is located on a hub 40, which is centrally located in the interior of the closed container, and which extends between the interior surfaces of the front faced 12 and the back face 14, in the region occupied by the hub 40. Clearly, as can be seen in FIGS. 4 and 7, for example, the reel of dental floss 24 is mounted for rotation about the hub 40 when the dental floss is unwound and removed from the reel.

As seen in FIGS. 1 to 4, a strand of dental floss 42 is unreeled from the reel of dental floss 24. The strand of dental floss 42 extends through an opening 44. The opening 44 is formed in a first corner of the front face 12; so that the first corner can be said to be defined by the opening 44 in that it is the corner at which the opening is located.

There is a friction and cutting member located at a second corner of the front face. As described above, the second corner may be diagonally opposed to the first corner or it may be adjacent the first corner. In any event, the friction and cutting member 50 comprises a tongue portion 52 which is angled away from a base portion 54—see FIGS. 4 and 6, in particular.

The front face is concave on an axis 25 (see FIG. 3) which extends between a pair of diagonally opposed corners of the container. The concavity is particularly illustrated in FIGS. 2 and 4. The concavity is defined by ridges which are formed in the front face at the first corner and at the corner which is diagonally opposed to the first corner. Those ridges are identified in FIGS. 2 and 4, in particular, at 60 and 62.

Figure 2:
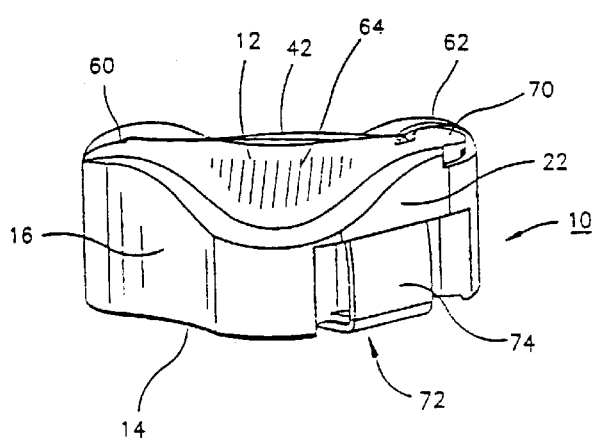
FIG. 2 is a side view of the embodiment of FIG. 1.

There is also a C-shaped chute 70 which is formed at the second corner, and it is positioned such that the dental floss extends from the opening 44 to the C-shape chute 70, particularly as shown in FIGS. 1 and 2.

Figure 3:
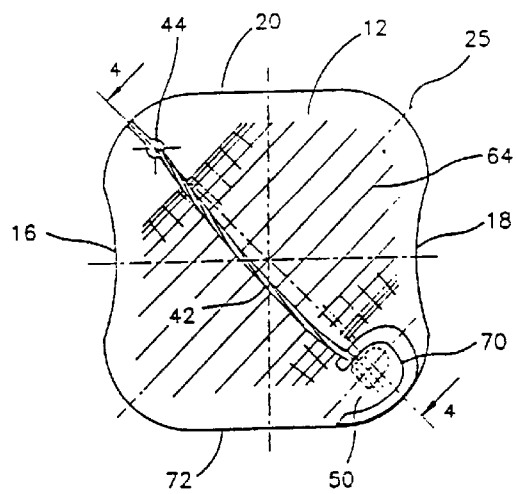
FIG. 3 is a plan view of the embodiment of FIG. 1, looking at the front face thereof.

In most embodiments of the present invention, the friction and cutting member 50 is secured in place in the interior of the container, as shown particularly in FIGS. 3, 4, and 6. In such instance, the friction and cutting member 50 is secured in place at the second corner and at the interior surface of the front face 12. Particularly in the embodiment FIGS. 1 to 4, 6, and 7, the friction and cutting member is located in the ridge 62 at the second corner, so that it is located in the bight of the C formed by the C-shaped chute 70.

Typically, any dental floss dispenser in keeping with the present invention is comprised of a container which is molded from a suitable plastics material, as will be evident to persons skilled in the art; and the friction and cutting member is formed from metal, usually by stamping.

Another feature of the present invention is that there may be, indeed, a plurality of ridges 64 which are formed in the front face 12 of the container. The ridges 64 are formed in a direction parallel to the axis 25, and assist in guiding the finger of the user across the concave front face as dental floss is withdrawn from the interior of the dental floss dispenser.

To assist further in guiding dental floss through the opening 44 as is unreeled from the reel 24, a guide wall 66 may be formed in the interior of the dispenser, extending inwardly from the interior surface of the front face 12 in the vicinity of the opening 44 at the first corner. The guide wall 66 is positioned inwardly from the opening 44, towards the hub 40.

Finally, a further aspect of the present invention is discussed. That is, any dental floss dispenser in keeping with the present invention may further comprise adhesive means 72 disposed on the substantially planar back face 14. The adhesive means 72 provides means whereby the dental floss dispenser of the present invention may be adhesively mounted to a mounting surface. Such mounting surface may be any convenient, substantially planar surface, such as a counter top, the side wall of a drawer, etc.; however, most usually, the mounting surface is a vertical surface such as a bathroom mirror, the inside surface of the door of a medicine cabinet, and so on.

Typically, the adhesive means 72 is a flexible flat plastic tape, which has an adhesive coating on at least a portion of each of the two sides thereof. The coating on the surface of the flexible plastic tape which is adjacent the back face 14 of the container thereby adheres the adhesive means 72 to the dental floss dispenser. The adhesive on the other side of the flexible tape is generally provided with a release cover (not shown) whereby the dental floss dispenser may be adhered to a mounting surface when desired, but not until. This is clear, for example, from an examination of FIGS. 4, 5, and 7.

Also, typically, the flexible plastic tape which comprises the adhesive means 72 is formed so as to have a second portion on each of the two sides thereof which has no adhesive coating thereon. This uncoated portion of the flexible plastic tape thereby forms a graspable tab 74 which may be grasped by the fingers so as to facilitate the removal of the dispenser from a mounting surface when it is adhered thereto. Such removal would occur, for example, when the reel of dental floss 24 in the interior of the dental floss dispenser has been exhausted so that it is necessary to replace the dental floss dispenser with a new one—or in some instances, to replace the reel of dental floss inside the dental floss container.

A particular flexible plastic tape having the characteristics as described above is one which is brought to the market by 3-M Company in association with its trade mark COMMAND™.

Turning now to FIG. 8, a particular embodiment 80 of dental floss dispenser in keeping with the present invention is shown. In this case, however, the first and second corners are adjacent one another rather than being diagonally opposed to one another. Accordingly, in this embodiment, as the finger sweeps across the entire front surface 12, along the ridges 64 if they are present, there may be a larger loop of dental floss 42 which is formed at the end of the finger before the dental floss is grasped between the fingers so as to be withdrawn from the interior of the container. Thus, somewhat less manual dexterity may be necessary, such as for individuals who suffer from arthritis.

In all events, and in any embodiment of dental floss dispenser in keeping with the present invention, once a loop of dental floss 42 has been formed by essentially dragging the finger across the front surface 12 of the container, and grasping the dental floss between the finger and thumb for example, it is easy to cut off a required length of dental floss simply by placing the portion of dental floss closest to the opening 44 through the C-shaped chute 70. Then, whether the friction and cutting member 50 is interiorly located, as would be the usual case, or is exteriorly located as might be the case, the cutting of the dental floss in the usual manner may be easily accomplished. Of course, the end of the dental floss 42 which remains in the friction and cutting member 50 remains held in place as a consequence of the structure of the friction and cutting member, with the tongue portion 52 being angled away from the base portion 54 in the well known manner.

There has been described a dental floss dispenser which may be inexpensively provided to the market, and particularly which may be mounted on a surface in the user's bathroom so as promote diligent daily flossing practices.

Throughout this specification and the claims which follow, unless the context requires otherwise, the word "comprise", and variations such as "comprises" or "comprising", will be understood to imply the inclusion of a stated integer or step or group of integers or steps but not to the exclusion of any other integer or step or group of integers or steps.

For example substantially planar means exhibiting the characteristics of planarity or flatness, or of being on the same plane, without necessarily being restricted to that preciseness of meaning.

What is claimed is:

1. A dispenser for dental floss comprising:

a closed container having a reel of dental floss disposed therein, said container having a generally planar back face, a front face, a pair of opposed side faces, a top face, a bottom face opposed to said top face, and a corner at each intersection of said top and bottom faces with said pair of opposed side faces.

a hub centrally located in the interior of the closed container and extending between the interior surfaces of said front and back faces, in the region occupied by said hub, and a reel of dental floss being mounted for rotation about said hub when said dental floss is unwound and removed from said reel;

on opening in said front face at a first corner thereof, through which opening a strand of dental floss extends so as to be unwound from said reel;

a C-shaped chute formed at a second corner, and being positioned such that said dental floss extends from said opening at said first corner through said C-shaped chute located at said second corner; and a friction and cutting member at said second corner of said front face;

wherein said friction and cutting member comprises a tongue portion which is angled away from a base portion thereof, and is secured in place at said second corner thereof; and wherein said front face is concave on an axis extending between a pair of diagonally opposed corners of said container, the concavity thereof being defined by ridges formed in said front face at said first corner and at a corner thereof which is diagonally opposed to said first corner.

2. The dental floss dispenser of claim 1, wherein said corner is adjacent said first corner.

3. The dental floss dispenser of claim 2, wherein said friction and cutting member is secured in place in the interior of said container at said corner thereof at the interior surface of said front face.

4. The dental floss dispenser of claim 3, wherein said friction and cutting member is located in the bight of the C.

5. The dental floss dispenser of claim 3, further comprising adhesive means on the substantially planar back face, whereby said dental floss dispenser may be adhesively mounted to a mounting surface.

6. The dental floss dispenser of claim 5, wherein said adhesive means comprises a flexible plastic tape having an adhesive coating on at least a portion of each of the two sides thereof.

7. The dental floss dispenser of claim 6, wherein said flexible plastic tape is stretchable, and wherein a second portion on each of the two sides thereto has no adhesive coating thereon; and wherein the uncoated portion of the flexible plastic tape forms a graspable tab to facilitate removal of said dispenser from a mounting surface when adhered thereto.

8. The dental floss container of claim 5, wherein said dental floss dispenser may be adhesively mounted to a vertical surface.

9. The dental floss dispenser of claim 2, wherein the front face of said container has a plurality of ridges formed therein in a direction parallel to said axis.

10. The dental floss dispenser of claim 1, wherein said second corner is diagonally opposed to said first corner.

11. The dental floss dispenser of claim 10, wherein said friction and cutting member is secured in place in the interior of said container at said second corner thereof at the interior surface of said front face.

12. The dental floss dispenser of claim 11, wherein said concavity of said front face is defined by ridges formed in said front face at said first and second corners thereof, wherein said C-shaped chute is formed in the ridge at said second corner, and wherein said friction and cutting member is located in the bight of the C.

13. The dental floss dispenser of claim 11, further comprising adhesive means on the substantially planar back face, whereby said dental floss dispenser may be adhesively mounted to a mounting surface.

14. The dental floss dispenser of claim 13, wherein said adhesive means comprises a flexible plastic tape having an adhesive coating on at least a portion of each of the two sides thereof.

15. The dental floss dispenser of claim 13, wherein said flexible plastic tape is stretchable, and wherein a second portion on each of the two sides thereof has no adhesive coating thereon; and wherein the uncoated portion of the flexible plastic tape forms a graspable tab to facilitate removal of said dispenser from a mounting surface when adhered thereto.

16. The dental floss container of claim 13, wherein said dental floss dispenser may be adhesively mounted to a vertical surface.

17. The dental floss dispenser of claim 10, wherein the front face of said container has a plurality of ridges formed therein in a direction parallel to said axis.

18. The dental floss dispenser of claim 1, wherein said container is molded from a plastics material, and said friction and cutting member is formed from metal.

19. The dental floss dispenser of claim 1, further comprising a guide wall extending inwardly from the interior surface of said front face in the vicinity of said opening at said first corner, and being positioned inwardly from said opening towards said hub.

* * * * *